(12) United States Patent
Ronchi et al.

(10) Patent No.: US 10,568,550 B2
(45) Date of Patent: Feb. 25, 2020

(54) METHOD AND APPARATUS FOR MEASURING REACTION FORCES

(71) Applicant: DORSAVI LTD, Melbourne East, Victoria (AU)

(72) Inventors: Daniel Matthew Ronchi, Victoria (AU); Andrew James Ronchi, Victoria (AU); Edgar Charry, Victoria (AU); Aakanksha Chhikara, Victoria (AU); Wenzheng Hu, Victoria (AU)

(73) Assignee: DORSAVI LTD, East Melbourne (AU)

( * ) Notice: Subject to any disclaimer, the term of this patent is extended or adjusted under 35 U.S.C. 154(b) by 0 days.

(21) Appl. No.: 14/419,909

(22) PCT Filed: Jul. 24, 2013

(86) PCT No.: PCT/AU2013/000814
§ 371 (c)(1),
(2) Date: Feb. 5, 2015

(87) PCT Pub. No.: WO2014/022877
PCT Pub. Date: Feb. 13, 2014

(65) Prior Publication Data
US 2015/0201868 A1    Jul. 23, 2015

(30) Foreign Application Priority Data

Aug. 7, 2012   (AU) ................ 2012903399

(51) Int. Cl.
*A61B 5/11*   (2006.01)
*A61B 5/00*   (2006.01)
(Continued)

(52) U.S. Cl.
CPC .......... *A61B 5/1122* (2013.01); *A61B 5/6828* (2013.01); *A61B 5/7225* (2013.01);
(Continued)

(58) Field of Classification Search
CPC ... A61B 5/1036; A61B 5/1114; A61B 5/1123; A61B 2562/0219; A61B 5/11;
(Continued)

(56) References Cited

U.S. PATENT DOCUMENTS 7,756,607 B2 * 7/2010 Ikeuchi ................ B62D 57/032
                                                                         700/245
8,363,891 B1   1/2013 Weyand et al.
(Continued)

FOREIGN PATENT DOCUMENTS

CN    1520350 A    8/2004
CN    1561908 A    1/2005
(Continued)

OTHER PUBLICATIONS

Elvin, Niell, et. al. "Correlation between Ground Reaction Force and Tibial Acceleration in Vertical Jumping." *Journal of Applied Biomechanics*, vol. 23, No. 3, 2007, pp. 180-189.
(Continued)

*Primary Examiner* — Nimeshkumar D Patel
*Assistant Examiner* — Nashmiya S Fayyaz
(74) *Attorney, Agent, or Firm* — Mintz, Levin, Cohn, Ferris, Glovsky and Popeo, P.C.

(57) ABSTRACT

Apparatus is disclosed for monitoring, measuring and/or estimating a force applied to a body or body part of a vertebral mammal. The apparatus includes an acceleration sensor for measuring acceleration of the body or body part relative to an inertial frame of reference and for providing data indicative of the acceleration. The acceleration sensor includes at least one inertial sensor, a memory device adapted for storing the data, and a processor adapted for processing the data to evaluate a reaction force that correlates to the data. The processor may be configured to execute an algorithm for evaluating the reaction force, based on one
(Continued)

or more correlation components such as mass, speed and/or velocity associated with the body or body part. A method of monitoring and/or estimating a force applied to a body or body part of a vertebral mammal is also disclosed.

30 Claims, 6 Drawing Sheets

(51) Int. Cl.
G01L 1/00 (2006.01)
G01P 15/00 (2006.01)
(52) U.S. Cl.
CPC .............. *A61B 5/7246* (2013.01); *G01L 1/00* (2013.01); *G01P 15/00* (2013.01); *A61B 5/112* (2013.01); *A61B 2560/0223* (2013.01); *A61B 2560/0475* (2013.01); *A61B 2562/0219* (2013.01)
(58) Field of Classification Search
CPC ..... A61B 5/112; A61B 5/6828; A61B 5/7225; A61B 5/7246; A61B 2560/0223; A61B 2560/0475; A61B 2560/0219; G01P 11/00; G01P 15/00; G06K 9/00342; G01L 1/00
USPC .......................................... 73/865.4; 600/595
See application file for complete search history.

(56) References Cited

U.S. PATENT DOCUMENTS

| 2004/0107780 | A1  | 6/2004 | Kawai et al. |
| 2004/0116836 | A1* | 6/2004 | Kawai ................ B62D 57/032 |
| | | | 600/595 |
| 2004/0167641 | A1  | 8/2004 | Kawai et al. |
| 2007/0061106 | A1  | 3/2007 | Vock et al. |
| 2007/0073514 | A1  | 3/2007 | Nogimori et al. |
| 2009/0198155 | A1  | 8/2009 | Bonnet |
| 2010/0234769 | A1  | 9/2010 | Poliac et al. |
| 2011/0140897 | A1  | 6/2011 | Purks et al. |
| 2011/0181420 | A1  | 7/2011 | Mack et al. |

FOREIGN PATENT DOCUMENTS

| JP | 2012502721 A | 2/2012 |
| WO | WO-2011/157607 A1 | 12/2011 |
| WO | WO-2012/106770 A1 | 8/2012 |

OTHER PUBLICATIONS

Tran, J., et. al. "Validation of Accelerometer Data for Measuring Impacts During Jumping and Landing Tasks." *Proceedings of the 28th International Conference on Biomechanics in Sports* (Jan. 2010), International Society of Biomechanics in Sports, Konstanz, Germany, pp. 1-4.

* cited by examiner

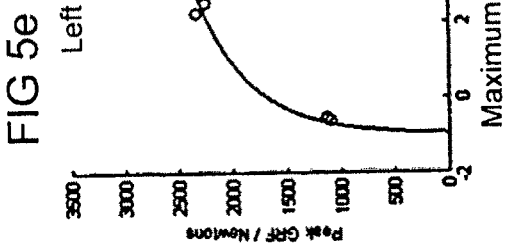
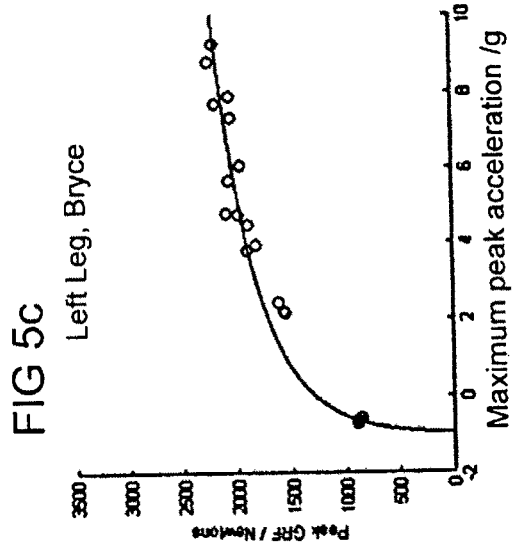
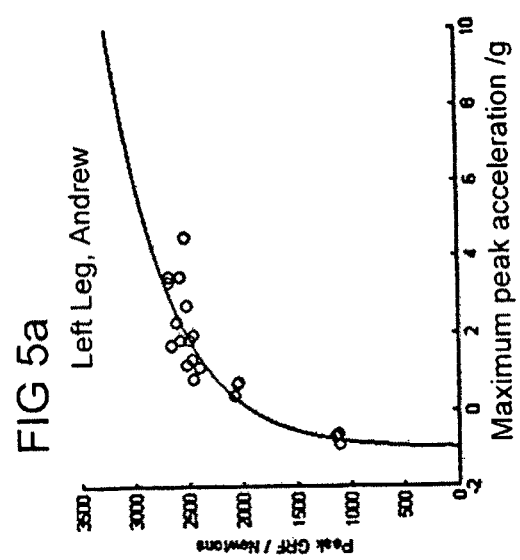
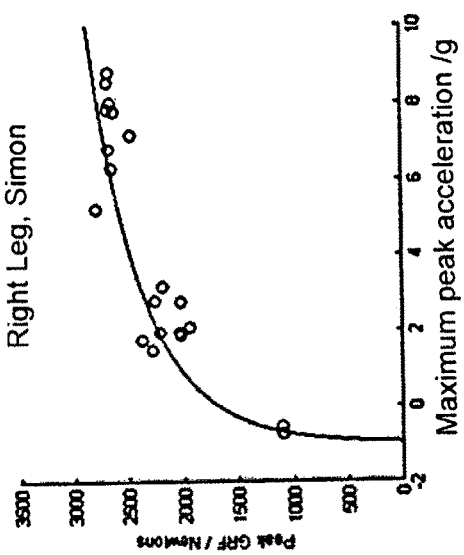
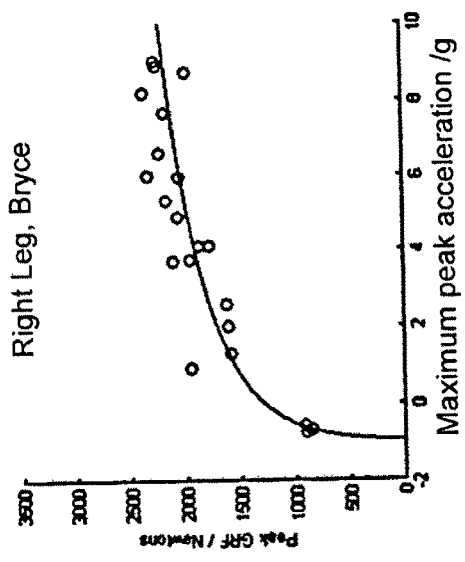
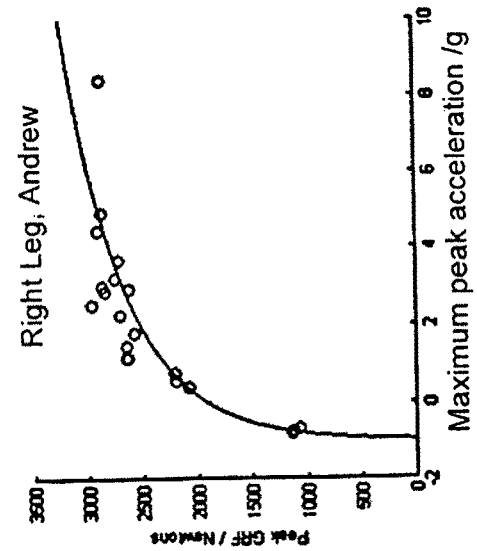
FIG 5a Left Leg, Andrew
FIG 5b Right Leg, Andrew
FIG 5c Left Leg, Bryce
FIG 5d Right Leg, Bryce
FIG 5e Left Leg, Simon
FIG 5f Right Leg, Simon

METHOD AND APPARATUS FOR MEASURING REACTION FORCES

FIELD OF THE INVENTION

The current application is a national-phase entry of Patent Cooperation Treaty application no. PCT/AU2013/000814, which has an international filing date of Jul. 24, 2013, and which claims the priority of Australian patent application no. 2012903399, filed on Aug. 7, 2012. The specifications, claims, and figures of both the PCT and Australian applications are incorporated herein by reference in their entireties.

The method and apparatus of the present invention may be used for comparing ground reaction forces measured with a force plate and sensors placed on a body of a mammal.

BACKGROUND OF THE INVENTION

In many applications that relate to measurement and assessment of ground reaction forces, such as rehabilitation, sports assessment, as well as design and construction of work places, an ability to make assessments about an activity may be improved by knowing the force or forces exerted on a limb or body part during its collision with a surface. This is because excessive forces acting on the limb(s), joint(s) or body part(s) during the collision may lead to injuries and/or damage to the limb(s), joint(s) or body part(s). Knowing the force or forces exerted on the limb(s), joint(s) or body part(s) may also enable symmetry/asymmetry between the forces to be computed. In one study an asymmetry index has been correlated with risk of injury.

A number of mechanical and/or physiological and/or biomechanical changes may occur when for example a limb or body part of a mammal such as a foot collides with a relatively hard surface such as the ground. In a mechanical/biomechanical context, the forces exerted during the collision may lead to sudden displacement of a part or parts of the limb or body part involved in the collision causing external and/or internal damage to the structure of the limb or body part of the mammal.

Some surfaces may be relatively more resilient and different surfaces may cause the limb(s), joint(s) or body part(s) to experience different forces. In a similar way, different techniques of running, different speeds, different shoes, gait patterns may also influence forces experienced by the body part(s). Forces may also be measured on a whole body such as the body of a mammal landing on a water or snow surface. This may have implications for assessing ski jumpers landing on a snow surface. In one example forces may be measured on a worker's wrist/hand striking a surface in order to help align parts, such as a vehicle assembly worker striking a die component to push it into place with possible implications for assessing workplace injuries.

Ground reaction forces have traditionally been measured via force platforms or force plates such as force plates manufactured by Advanced Mechanical Technology Inc. (AMTI). The measurements have been used to quantify ground reaction forces (GRFs), balance, gait and/or other parameters of biomechanics. Such measurements have been useful in areas of application such as medicine and sports. However such measurements are currently restricted to laboratory conditions since force platforms do not generally allow for a comprehensive measurement of parameters of biomechanics outside the laboratory or a tightly controlled setting. Force plate data is available in some specialist treadmills, but fundamentally changes running forces because the ground is moving under the subject. They also fail to provide an ability to measure forces on different terrains, slopes, cambers etc.

The present invention may alleviate the disadvantages of the prior art and/or may improve accuracy and/or validity and/or functionality and/or availability of GRF data. The present invention may also provide an ability to measure force data in virtually any setting, out in the field.

A reference herein to a patent document or other matter which is given as prior art is not to be taken as an admission that that document or matter was known or that the information it contains was part of the common general knowledge in Australia or elsewhere as at the priority date of any of the disclosure or claims herein. Such discussion of prior art in this specification is included to explain the context of the present invention in terms of the inventor's knowledge and experience.

Throughout the description and claims of this specification the words "comprise" or "include" and variations of those words, such as "comprises", "includes" and "comprising" or "including, are not intended to exclude other additives, components, integers or steps.

SUMMARY OF THE INVENTION

According to one aspect of the present invention there is provided apparatus for monitoring, measuring and/or estimating a force applied to a body or body part of a vertebral mammal, said apparatus including:

an acceleration sensor for measuring acceleration of said body or body part relative to an inertial frame of reference and for providing data indicative of said acceleration, wherein said acceleration sensor includes at least one inertial sensor;

a memory device adapted for storing said data; and a processor adapted for processing said data to evaluate a reaction force that correlates to said data.

According to a further aspect of the present invention there is provided a method of monitoring, measuring and/or estimating a force applied to a body or body part of a vertebral mammal, said method including:

using at least one inertial sensor to measure acceleration of said body or body part relative to an inertial frame of reference and to provide data indicative of said acceleration;

storing said data in a memory device; and processing said data by a processor to evaluate a reaction force that correlates to said data.

The processor may be configured to execute an algorithm for evaluating the reaction force. The algorithm may be adapted to cause the processor to evaluate the reaction force based on one or more correlation components including mass, speed and/or velocity associated with the body or body part.

The processor may be configured to process the data according to a relationship function such as a non-linear relationship function between the acceleration data and the reaction force. The relationship function may be substantially logarithmic and may include one or more calibration coefficients. The processor may be adapted to process the data by equalizing the one or more calibration coefficients.

In one form the processor may be adapted to provide a correlation with a reaction force $GRF_{Peak}(acc,m)$ according to the following equation:

$$GRF_{Peak}(acc,m) = a(m) * [\log_2(acc+b)] + c(m)$$

wherein:

m denotes mass of a mammal subject;

acc denotes acceleration data measured by the acceleration or inertial sensor;

"a" denotes a slope of a logarithmic function;

"b" is a fixed coefficient to compensate accelerations lower than 0 g; and

"c" denotes an offset associated with the logarithmic function.

In one form a(m)=4.66*m−76.60; and c(m)=24.98*m−566.83. The slope a of the logarithmic function may include a linear function of the body mass of the subject. In one form coefficient b may be set to 1. In one form offset c may include a linear function of the body mass.

In a preferred embodiment the reaction force provided by the processor may be substantially comparable or equivalent to a ground reaction force measured by an AMTI force plate.

The at least one inertial sensor may include an accelerometer. The accelerometer may be adapted for measuring acceleration along one or more orthogonal axes.

The body of the mammal subject may include limbs such as legs and in one application the apparatus may be adapted to monitor acceleration components associated with forces applied to the legs. Respective acceleration sensors may be applied to the legs of the mammal.

In other applications the apparatus may be adapted to monitor acceleration components associated with a force or forces applied to other limbs such as an arm or arms or to monitor acceleration components associated with a force applied to the whole body. In those events the acceleration sensor may be applied to the arm or arms or to a position on the body suitable for monitoring acceleration of the body as a whole.

The each inertial sensor may include or be associated with an analog to digital (A to D) converter for converting analog data to a digital domain. The A to D converter may be configured to convert an analog output from the acceleration sensor to the data prior to storing the data.

The present invention may include apparatus suitable for monitoring a force(s) exerted on a limb or body part of a mammal during a collision. The present invention may further include a method for using data from the apparatus to ascertain the force(s) exerted on the limb or body part during the collision. The apparatus may include sensors for placing on the limb, such a leg or legs of a human subject and hardware and/or software components for monitoring and/or determining a ground reaction and/or collision force experienced when the foot strikes a surface during activities such as walking, running, sprinting, hopping, landing and/or jumping. The apparatus may include a digital processing engine and one or more algorithms for processing variables such as body weight or mass of the subject, pattern of movement including gait pattern and/or surface type to more accurately determine the ground reaction or collision force.

The apparatus of the present invention may facilitate monitoring of reaction force(s) in a variety of environments including indoor and/or outdoor environments for diverse purposes including but not limited to applications such as monitoring and/or measuring ground reaction force(s) experienced by an athlete, for preventing or at least minimizing incidence of injuries and/or to provide guidance in adopting optimal and/or symmetrical techniques to improve athletic performance.

DESCRIPTION OF THE DRAWINGS

FIGS. 5(a) to 5(f) show logarithmic approximations for three subjects (Andrew, Bryce, Simon) of acceleration data to peak ground reaction forces.

DESCRIPTION OF A PREFERRED EMBODIMENT

As described above ground reaction forces (GRFs) are traditionally measured via force platforms or force plates such as force plates manufactured by AMTI. Also as described such measurements are currently limited to laboratory conditions since force platforms do not generally allow for a comprehensive measurement of parameters of biomechanics in the field or outside of the laboratory.

The apparatus and method of the present invention may be suitable for monitoring and/or ascertaining ground reaction force (GRF) without using force platforms or force plates and as such may be suitable for monitoring and/or ascertaining ground reaction forces (GRFs) in the field or outside of a tightly controlled setting.

The apparatus and method of the present invention is suitable for monitoring and/or ascertaining ground reaction force experienced by a human subject at a given point in time and it is described herein in this context. Nevertheless, it is to be appreciated that the present invention is not thereby limited to such applications.

Figure 1:
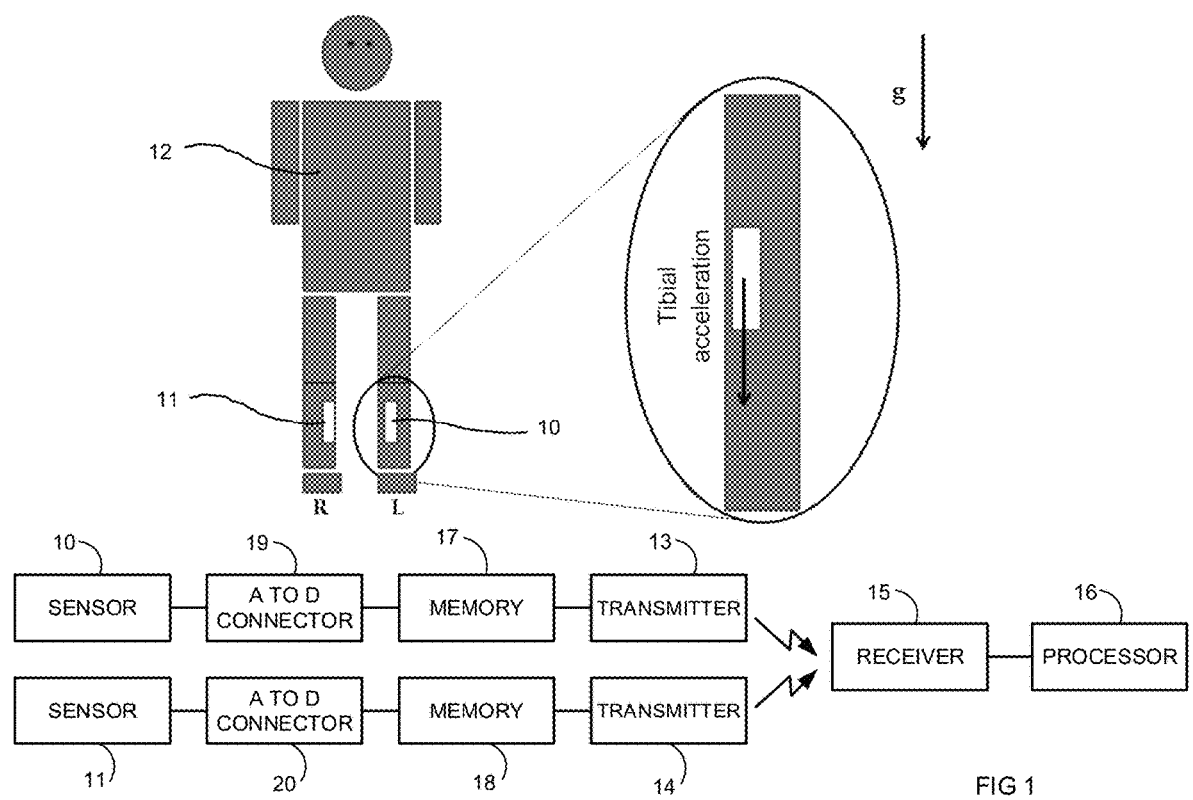
FIG. 1 shows one form of apparatus according to the present invention.

Referring to FIG. 1, one form of apparatus according to the present invention includes sensors 10, 11 placed along or in-line with tibial axes of the left and right legs of a human subject 12. Each sensor 10, 11 may include an inertial sensor such an accelerometer and/or a magnetic sensor such as a magnetometer to ascertain force(s) exerted on the legs of subject 12 during collision with a surface such a ground surface (not shown). The positive axes on both legs may point up or down so that tibial acceleration may be measured in a vertical direction at least. The or each collision with a surface experienced during activities such as walking, running, sprinting, hopping, landing and/or jumping will typically give rise to a ground reaction force.

Acceleration signals measured via sensors 10, 11 may be sent via wireless transmitters 13, 14 to remote receiver 15. Receiver 15 is associated with digital processing engine 16. Digital processing engine 16 includes a digital processor such as a microprocessor for processing data.

Digital processing engine 16 may include an algorithm for evaluating a correlation with a ground reaction force such as a ground reaction force that may be measured via a force platform or force plate. Digital processing engine 16 may perform calculations with the algorithm based on a substantially non-linear or logarithmic relationship between acceleration data obtained from sensors 10, 11 and the ground reaction force.

In one form a digital memory or data storing means 17, 18, may be associated with sensors 10, 11 for storing data in digital format for analysis and/or reporting. Digital memory 17, 18 may include structure such as flash memory, memory card, memory stick or the like for storing digital data. The memory structure may be removable to facilitate downloading the data to a remote processing device such as a PC or other digital processing engine.

The digital memory 17, 18 may receive data from sensors 10, 11. Each sensor 10, 11 may include or be associated with an analog to digital (A to D) converter 19, 20. The or each A to D converter 19, 20 and memory 17, 18 may be associated directly with sensors 10, 11 such as being located on the same printed circuit board (PCB) as sensors 10, 11 respectively. Alternatively sensors 10, 11 may output analog data to transmitters 13, 14 and one or more A to D converters may be associated with remote receiver 15 and/or digital processing engine 16. The one or more A to D converters may convert the analog data to a digital domain prior to storing the data in a digital memory such as a digital memory described above. In some embodiments digital processing engine 16 may process data in real time to provide biofeedback to subject 12 being monitored.

Figure 2:
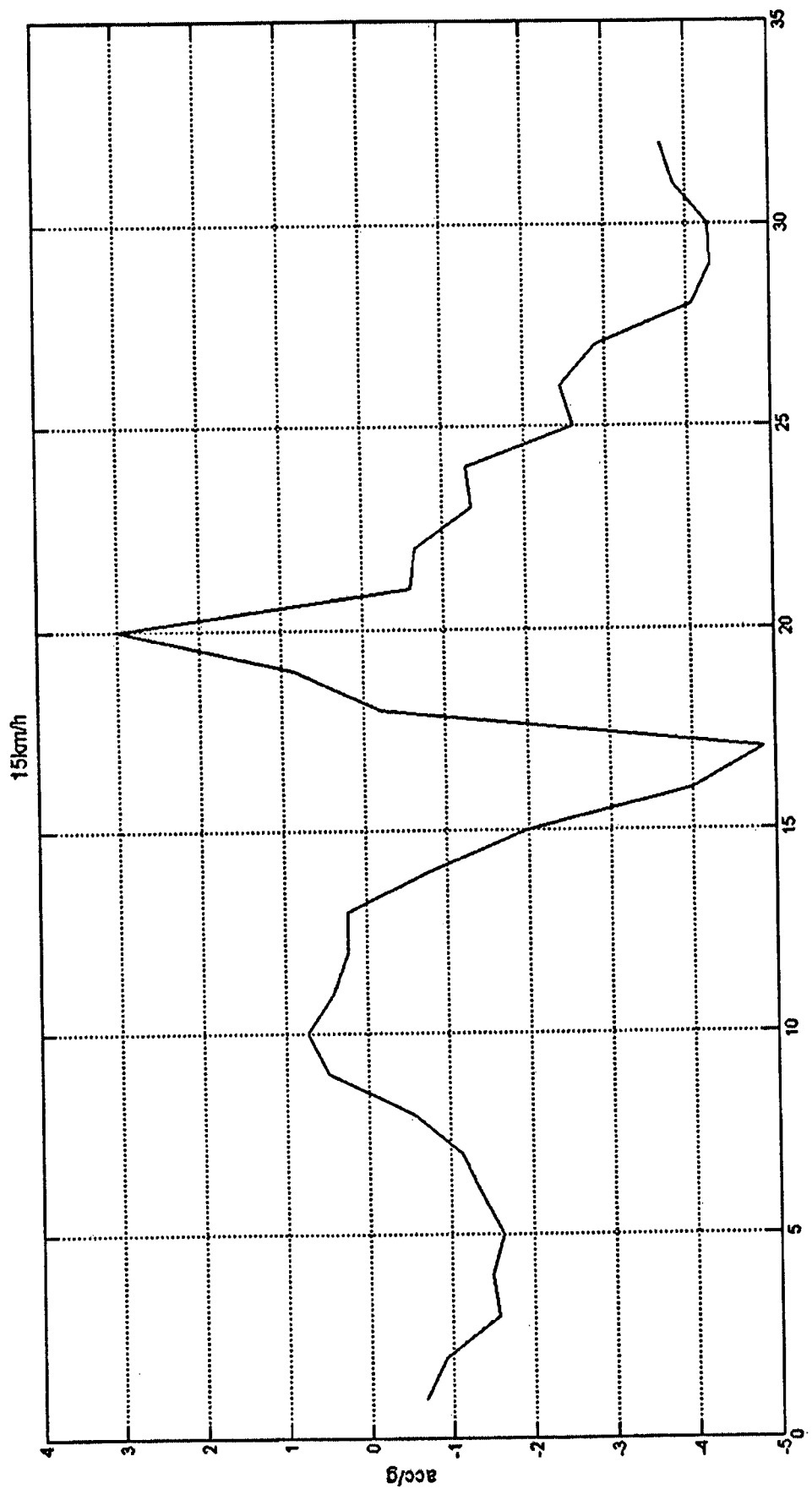
FIG. 2 shows typical tibial acceleration at running speed of 15 km/h for a subject with no history of injuries.

The accelerometer axis used in the present embodiment is the x-axis according to FIG. 1. The largest positive peak acceleration after the maximum negative peak in a stance phase (refer FIG. 2) may be measured along the x-axis, e.g. when subject 12 is running, due to good repeatability and high correlation with comparable peak ground reaction forces when these are measured by an AMTI force plate for the same subject 12 undertaking a similar task.

In another embodiment GRF may be calculated by using vertical and forward horizontal vectors to create a more accurate estimation of vertical GRF, based on the angle that the tibia makes with the ground at a point of maximum force. The horizontal vector may also provide an insight as to whether the subject is accelerating or decelerating.

It may be shown that correlation components between acceleration data and reaction force are essentially non-linear when taking into account variations in speed (6 km/h-26 km/h) and in body mass of subject 12. Hence, it may be shown that acceleration data may be correlated with peak ground reaction force according to the following equation:

$$GRF_{Peak}(acc,m)=a(m)*[\log_2(acc+b)]+c(m)$$

wherein:

"a" denotes a slope of a logarithmic function and is typically a linear function of the body mass m of subject 12;

"b" is a fixed coefficient (typically set to 1) to compensate accelerations lower than 0 g;

"c" denotes an offset associated with the logarithmic function and typically is a linear function of body mass m of subject 12;

$$a(m)=4.66*m-76.60; \text{ and}$$

$$c(m)=24.98*m-566.83$$

Figure 3:
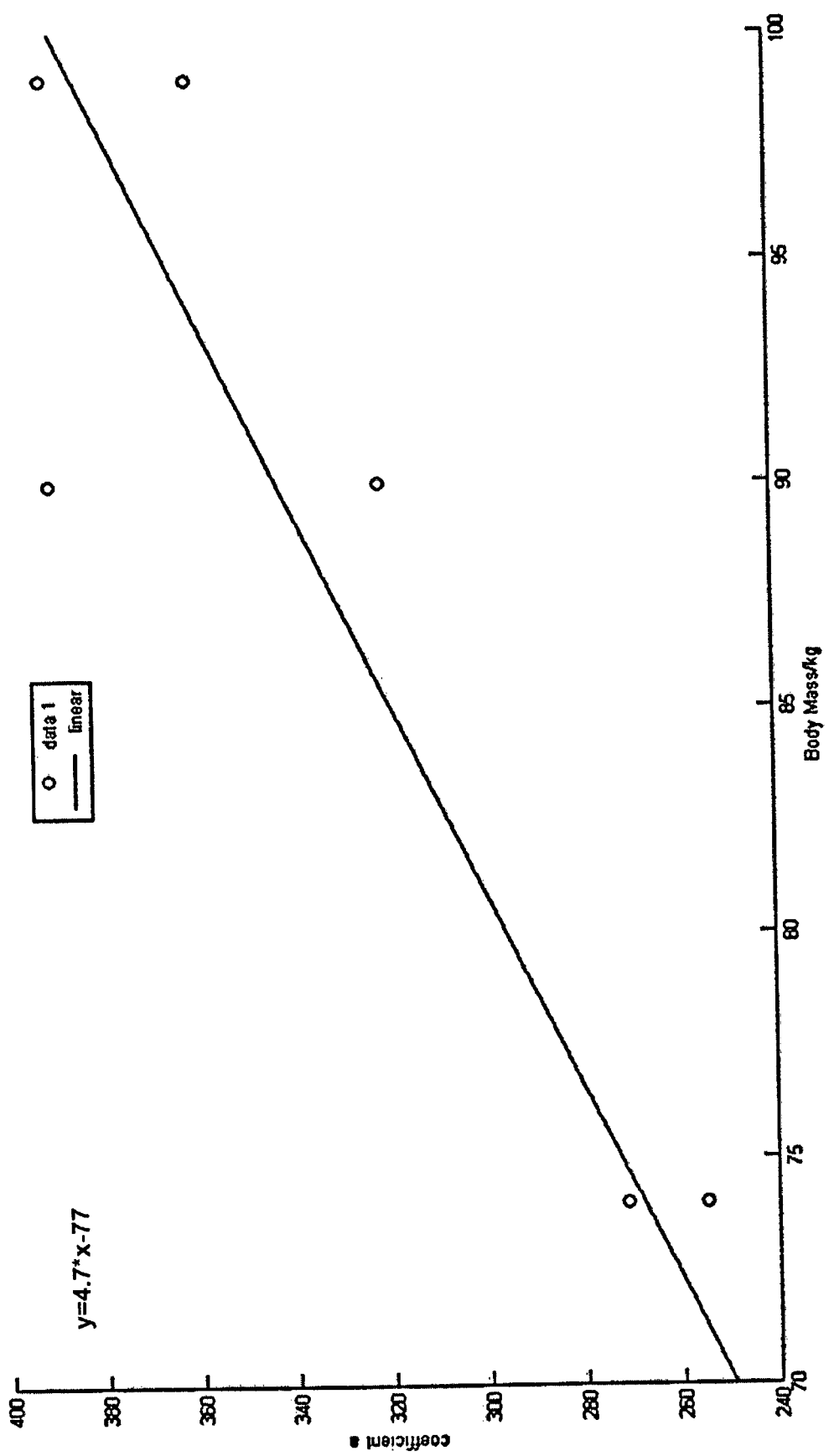
FIG. 3 shows coefficient "a" being modelled as a linear function between body mass and individual gains of linear equations for each subject.
Figure 4:
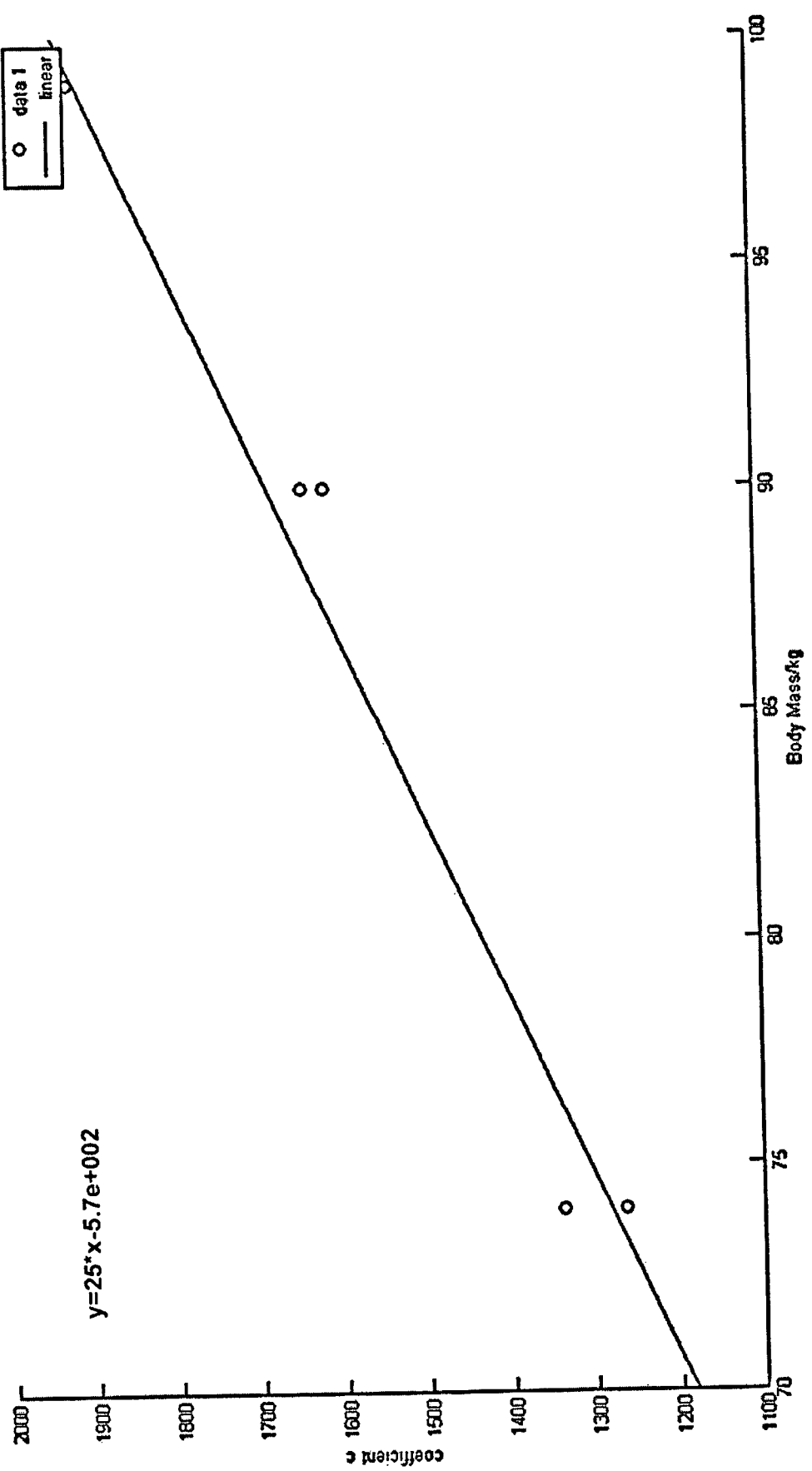
FIG. 4 shows coefficient "c" being modelled as a linear function between body mass and individual offsets of linear equations for each subject.
Figure 6A:
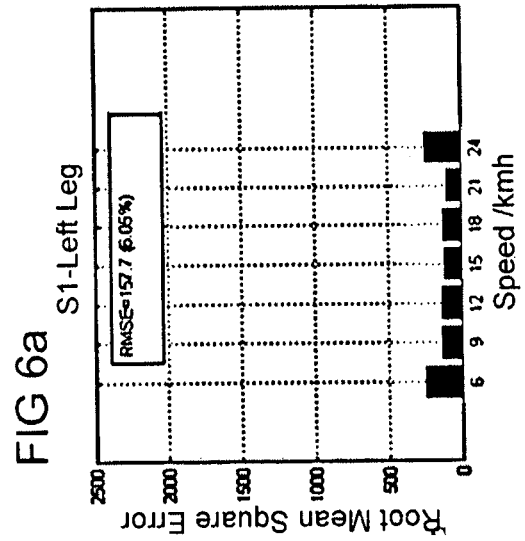
FIGS. 6(a) to 6(f) show RMSE for estimations of Ground Reaction Force for three subjects ($S_1$, $S_2$, $S_3$) when compared to a force plate.
Figure 6B:
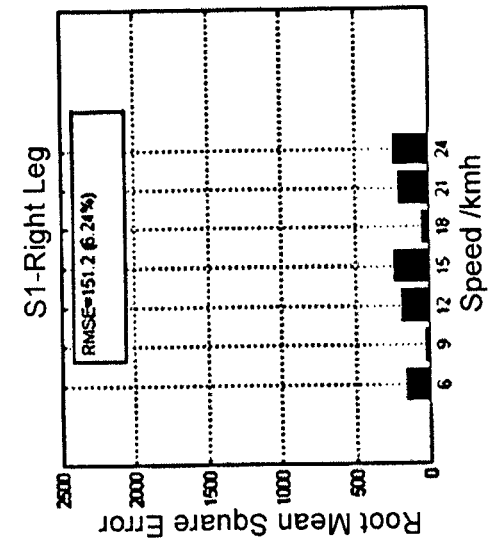
Figure 6C:
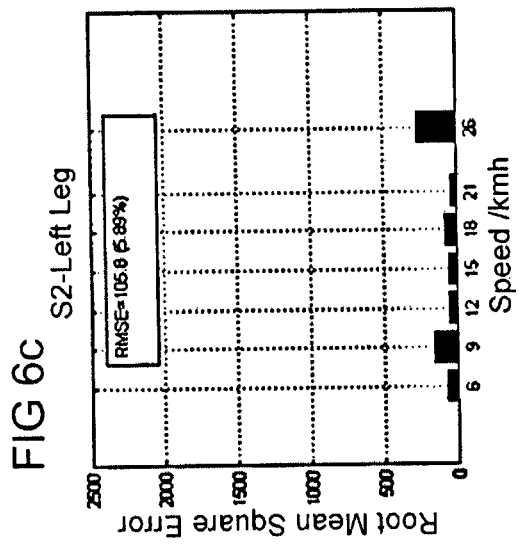
Figure 6D:
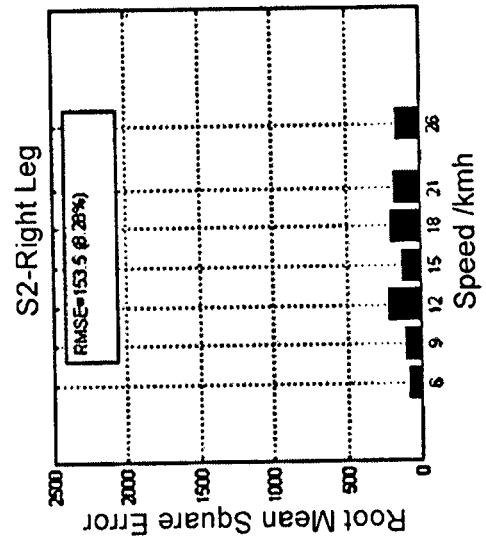
Figure 6E:
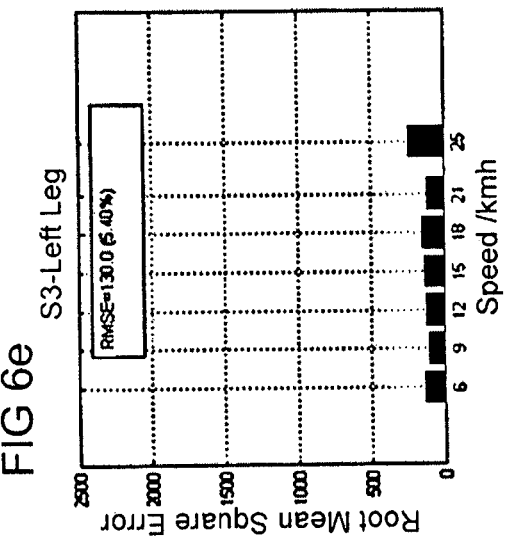
Figure 6F:
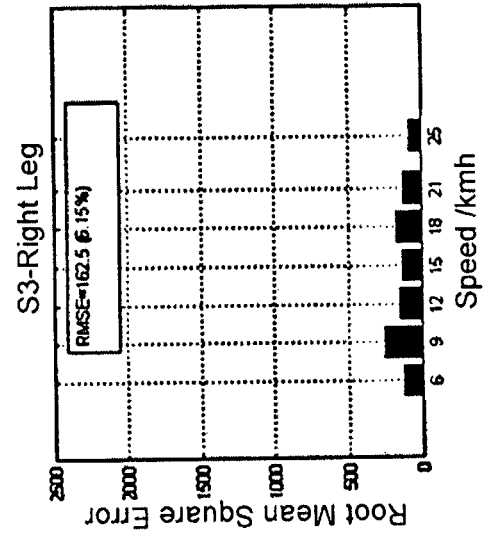

The two coefficients a(m) and c(m) may be assumed to be substantially linear functions with respect body mass m of subject 12 and are depicted in FIGS. 3 and 4 respectively. Initially, for each subject 12, a linear relationship between peak ground reaction forces and the peak accelerations may be estimated. For each equation (one per subject) gain and offsets may be modelled as a function of body mass of each subject. It was found that when such modelling was performed substantially linear approximation between individual gains and offsets correlated highly with the respective body masses leading to reduced error in estimating the ground reaction force.

The coefficient b includes a factor to avoid a negative logarithmic function. As peak accelerations may be small (<1 g) during walking speeds (6 km/h), this mathematical corrective factor may ensure that an estimated GRF is always positive. In some embodiments acceleration peaks may be averaged across several strides to reduce errors due to data delivery via wireless communications and/or to improve system stability.

The method described above was validated using an AMTI force plate. Estimated errors during validation testing using Root Mean Square Error (RMSE) are shown in FIG. 3, wherein errors in data from three subjects fell between 5.4% to 8.28% and the average error across three subjects was 6.33% for both legs over all speeds.

As noted above knowing the force or forces exerted on the limb(s), joint(s) or body part(s) may enable symmetry/asymmetry between forces to be computed. For example, the balance of forces being applied during different technique or equipment use, or the balance/symmetry of one leg striking the ground compared to the other may be computed.

An asymmetry index (ASI) may be calculated for a subject as follows:

$$ASI(\%)=100*(L-R)/((L+R)/2), \text{ wherein } L \text{ and } R \text{ correspond to measurements of}$$

GRF in Newtons unit from left and right limbs respectively of the subject.

Examples of ASI calculated for subjects 1 and 2 are shown below:

$$Subject 1: ASI(\%)=100*(2619-1930)/(2619+1930)/2)=30.3\%$$

$$Subject 2: ASI(\%)=100*(2496-2289)/((2496+2289)/2)=8.6\%"$$

Finally, it is to be understood that various alterations, modifications and/or additions may be introduced into the constructions and arrangements of parts previously described without departing from the spirit or ambit of the invention.

The invention claimed is:

1. Apparatus for monitoring, measuring and/or estimating a force applied to a body or body part of a vertebral mammal, said apparatus including:
    an acceleration sensor for measuring acceleration of said body or body part relative to an inertial frame of reference and for providing data indicative of said acceleration from a single sensor;
    a memory device adapted for storing said data; and
    a processor adapted for processing using only said data indicative of acceleration to evaluate a reaction force that correlates to said data, wherein said processor is configured to process said data indicative of acceleration according to a non-linear relationship function between said data and said reaction force, wherein said processor is configured to execute an algorithm for evaluating said reaction force, and wherein said algorithm is adapted to cause said processor to evaluate said reaction force based on one or more correlation coefficients including mass, speed and/or velocity associated with said body or body part, and wherein said relationship function is substantially logarithmic and includes said one or more correlation coefficients.

2. Apparatus according to claim 1 wherein said processor is adapted to provide a correlation with a reaction force $GRF_{Peak}(acc,m)$ according to the following equation:

$$GRF_{Peak}(acc,m)=a(m)*[\log_2(acc+b)]+c(m)$$

wherein:

m denotes mass of a mammal subject;

acc denotes acceleration data measured by the acceleration sensor;

"a" denotes a slope of a logarithmic function;
"b" is a fixed coefficient to compensate accelerations lower than 0 g; and
"c" denotes an offset associated with the logarithmic function.

3. Apparatus according to claim 2 wherein:

$a(m)=4.66*m-76.60$, and $c(m)=24.98*m-566.83$.

4. Apparatus according to claim 2 wherein the slope of the logarithmic function includes a linear function of the body mass of said subject.

5. Apparatus according to claim 2 wherein the coefficient b is set to 1.

6. Apparatus according to claim 1 wherein said reaction force provided by said processor is substantially comparable to a ground reaction force measured by an AMTI force plate.

7. Apparatus according to claim 1 wherein said acceleration sensor is adapted for measuring acceleration along one or more orthogonal axes.

8. Apparatus according to claim 1 wherein said body or body part of said mammal includes a leg and the apparatus is adapted to monitor acceleration components associated with forces applied to said leg.

9. Apparatus according to claim 1 wherein said acceleration sensor is applied to a leg of said mammal.

10. Apparatus according to claim 1 wherein said acceleration sensor includes an analog to digital (A to D) converter for converting analog data to a digital domain.

11. Apparatus according to claim 10 wherein said A to D converter is configured to convert an analog output from the acceleration sensor to said data prior to storing said data.

12. A method of monitoring, measuring and/or estimating a force applied to a body or body part of a vertebral mammal, said method including:
using an acceleration sensor to measure acceleration of said body or body part relative to an inertial frame of reference and to provide data indicative of said acceleration from a single sensor;
storing said data in a memory device; and
processing using only said data indicative of acceleration by a processor to evaluate a reaction force that correlates to said data, wherein said processor is configured to process said data indicative of acceleration according to a non-linear relationship function between said data and said reaction force, wherein said processor is configured to execute an algorithm for evaluating said reaction force, and wherein said algorithm causes said processor to evaluate said reaction force based on one or more correlation coefficients including mass, speed of and/or velocity associated with said body or body part, and wherein said relationship function is substantially logarithmic and includes said one or more correlation coefficients.

13. A method according to of claim 12 wherein said processor is adapted to provide a correlation with a reaction force $GRF_{Peak}(acc,m)$ according to the following equation:

$GRF_{peak}(acc,m)=a(m)*[\log_2(acc+b)]+c(m)$ wherein:
m denotes body mass of a mammal subject;
acc denotes acceleration data measured by said acceleration sensor;
"a" denotes a slope of a logarithmic function;
"b" is a fixed coefficient to compensate accelerations lower than 0 g; and
"c" denotes an offset associated with the logarithmic function.

14. A method according to claim 13 wherein:

$a(m)=4.66*m-76.60$; and $c(m)=24.98*m-566.83$.

15. A method according to claim 13 wherein the slope of said logarithmic function includes a linear function of the body mass of said subject.

16. A method according to claim 13 wherein the coefficient b is set to 1.

17. A method according to claim 12 wherein said reaction force provided by said processor is substantially comparable to a ground reaction force measured by an AMTI force plate.

18. A method according to claim 12 wherein said acceleration sensor is adapted for measuring acceleration along one or more orthogonal axes.

19. A method according to claim 12 wherein said body or body part of said mammal includes a leg and the method is adapted to monitor acceleration components associated with forces applied to said leg.

20. A method according to claim 12 wherein said acceleration sensor is applied to a leg of said mammal.

21. A method according to claim 12 wherein said acceleration sensor includes an analog to digital (A to D) converter for converting analog data to a digital domain.

22. A method according to claim 21 wherein said A to D converter is configured to convert an analog output from said acceleration sensor to said data prior to storing said data.

23. Apparatus for monitoring, measuring and/or estimating a force applied to a body or body part of a vertebral mammal, said apparatus including:
an acceleration sensor for measuring acceleration of said body or body part relative to an inertial frame of reference and for providing data indicative of said acceleration;
a memory device adapted for storing said data; and
a processor adapted for processing said data to evaluate a reaction force that correlates to said data, wherein said processor is adapted to provide a correlation with a reaction force GRFPeak(acc,m) according to the following equation:

$GRFPeak(acc,m)=a(m)*[\log_2(acc+b)]+c(m)$ wherein:
m denotes body mass of a mammal subject;
acc denotes acceleration data measured by the acceleration sensor;
"a" denotes a slope of a logarithmic function;
"b" is a fixed coefficient to compensate accelerations lower than 0 g; and
"c" denotes an offset associated with the logarithmic function.

24. Apparatus according to claim 23 wherein:

$a(m)=4.66*m-76.60$, and $c(m)=24.98*m-566.83$.

25. Apparatus according to claim 23 wherein the slope a of the logarithmic function includes a linear function of the body mass of said subject.

26. Apparatus according to claim 23 wherein the fixed coefficient b is set to 1.

27. A method of monitoring, measuring and/or estimating a force applied to a body or body part of a vertebral mammal, said method including:
using at least one acceleration sensor to measure acceleration of said body or body part relative to an inertial frame of reference and to provide data indicative of said acceleration;
storing said data in a memory device; and
processing said data by a processor to evaluate a reaction force that correlates to said data, wherein said processor is adapted to provide a correlation with a reaction force GRFPeak(acc,m) according to the following equation:

$$GRFPeak(acc,m) = a(m) * [\log_2(acc+b)] + c(m)$$

wherein:
m denotes body mass of a mammal subject;
acc denotes acceleration data measured by said at least one acceleration sensor;
"a" denotes a slope of a logarithmic function;
"b" is a fixed coefficient to compensate accelerations lower than 0 g; and
"c" denotes an offset associated with the logarithmic function.

28. A method according to claim 27 wherein:

$a(m) = 4.66*m - 76.60$; and $c(m) = 24.98*m - 566.83$.

29. A method according to claim 27 wherein the slope a of said logarithmic function includes a linear function of the body mass of said subject.

30. A method according to claim 27 wherein the fixed coefficient b is set to 1.

* * * * *